United States Patent [19]
Marchetti et al.

[11] Patent Number: 5,092,900
[45] Date of Patent: Mar. 3, 1992

[54] FEMUR HEAD PROSTHESIS

[75] Inventors: Pier G. Marchetti, Bologna, Italy; Roland Willi, Stadel; Rudolf Koch, Berlingen, both of Switzerland

[73] Assignees: Sulzer Brothers Limited, Winterthur; Protek AG, Berne, both of Switzerland

[21] Appl. No.: 665,338

[22] Filed: Mar. 6, 1991

[30] Foreign Application Priority Data

Mar. 13, 1990 [CH] Switzerland .................. 00798/90

[51] Int. Cl.$^5$ ............................................. A61F 2/32
[52] U.S. Cl. ............................................. 623/23
[58] Field of Search .................. 623/16, 18, 22, 23

[56] References Cited

U.S. PATENT DOCUMENTS 4,842,606  6/1989  Kranz et al.

FOREIGN PATENT DOCUMENTS 0196258 10/1986 European Pat. Off. ............ 623/23
0217034  4/1987 European Pat. Off. ............ 623/23
0273871  7/1988 European Pat. Off. ............ 623/23
3736304  5/1989 Fed. Rep. of Germany ........ 623/23

Primary Examiner—David J. Isabella
Assistant Examiner—Debra S. Brittingham
Attorney, Agent, or Firm—Kenyon & Kenyon

[57] ABSTRACT

A femur head prosthesis is provided with a shank body for implanting in a femur and a pair of removeably fastened cheeks which are secured to opposite sides at a proximal end of the shank body. The cheeks can be selected from a kit of different sized cheeks. Also, each cheek has a bulge extending laterally from the shank body. Also, each cheek tapers in conically from lateral to medial and from proximal to distal.

8 Claims, 3 Drawing Sheets

FEMUR HEAD PROSTHESIS

This invention relates to a femur head prosthesis.

As is known, for example from European patent applications 0 273 871; 0 217 034 and 0 196 258 as well as Swiss patents 671,689 and Swiss patent application No. 0385/88-3, femur head prostheses can be constructed of a common shank body and replaceable supporting bodies which enable individual adaption of the shank body to an existing bone cavity. By supplying the shank with a plurality of supporting bodies, a surgeon may be provided with the possibility of making a choice of supporting bodies during an implant operation.

Generally, in the case of femur head prostheses which are to be implanted in a bone without the use of bone cement, a problem arises in effecting a primary anchorage having plenty of contact area for the bone tissue without the bone tissue which later grows in becoming interrupted in certain zones in its blood supply through an excessive shear loading between the prosthesis and the bone tissue and, thus, withering.

Accordingly, it is an object of the invention to provide a femur head prosthesis with interchangeable parts adapted to a bone cavity while keeping a later settling of the prosthesis shank as small as possible.

Briefly, the invention provides a femur head prosthesis which is comprised of a shank body for implanting in a femur and a pair of cheeks which are removably fastened to opposite anterior (ventral) and posterior (dorsal) sides of a proximal end of the shank body. In accordance with the invention, each cheek has a bulge which extends laterally from the shank body and which tapers in conically from lateral to medial and from proximal to distal.

When putting together a femur head prosthesis for implanting in a bone cavity, the appropriate cheek may be chosen for size and for adaptation to the shape of the bone cavity which has been surgically prepared.

One advantage of the prosthesis resides in that the proximal end of the shank is centered on all sides by a cohesive area which tapers in conically towards the tip of the shank. This, at the same time, guarantees a uniform distribution of the main load on the prosthesis and allows a transfer of torque acting along the longitudinal axis. Moreover, the conical area is adaptable during the operation to correspond With the previously found conditions of the bone of the femur.

These and other objects and advantages of the invention will become more apparent from the following detailed description taken in conjunction with the accompanying drawings wherein.

Figure 2:
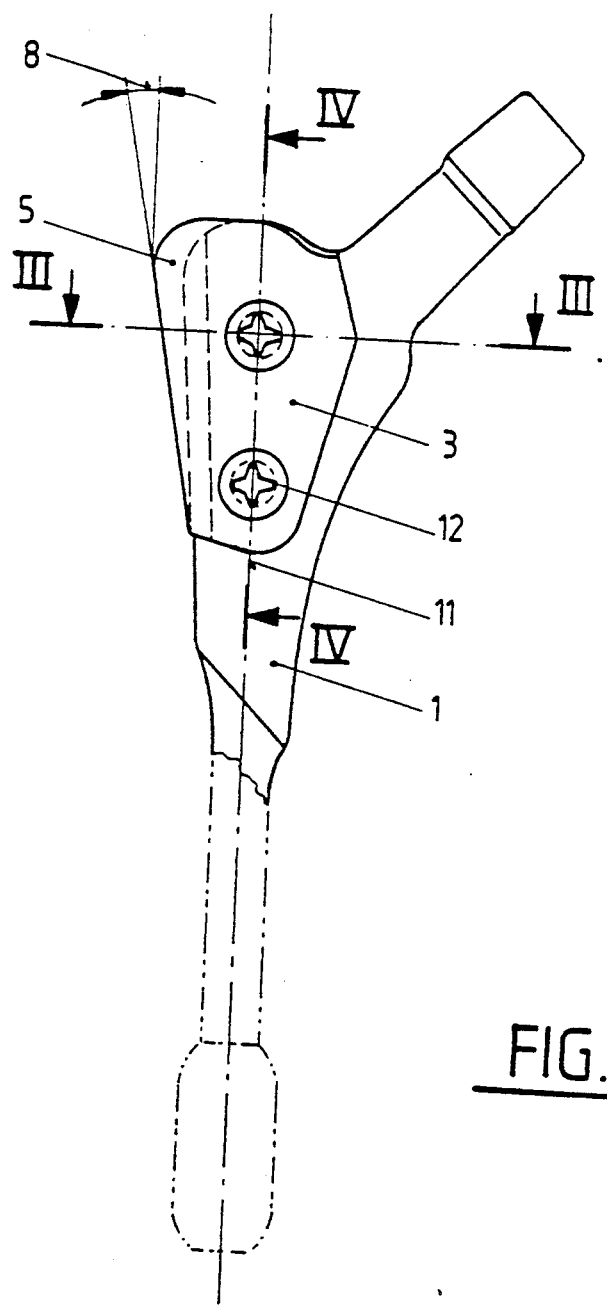
FIG. 2 illustrates a side view of a femur head prosthesis constructed in accordance with the invention.

Referring to FIG. 2, the femur head prosthesis is to be implanted in a bone without the use of bone cement and may be comprised of a uniform shank body 1 for implanting in the femur and various replaceable supporting bodies. Typical supporting bodies include replaceable shank tips (not shown). In addition, the prosthesis has a pair of cheeks 2, 3 (see FIG. 3) which are removably fastened to opposite ventral (anterior) and dorsal (posterior) sides of a proximal end of the shank body 1. Each cheek 2, 3 has a bulge 4, 5 which extends laterally from the shank body 1 and which tapers conically from lateral to medial and from proximal to distal. These cheeks 2, 3 are selected from a kit containing a plurality of cheeks which are graded in size by bulges which are of different sizes and conical tapers so that an appropriate pair of cheeks can be selected for implantation in a surgically prepared femur.

Referring to FIG. 2, the shank body 1 has a straight stem Which extends along a longitudinal axis 11. Looking in the direction of this axis 11 (see FIG. 3) the bulges 4, 5 of the respective cheeks 2, 3 stand out at the transition from dorsal or ventral to lateral and taper in conically towards the surface of the shank body both on the dorsal and ventral sides from lateral to medial and on the lateral, dorsal and ventral sides from proximal to distal. Laterally, the bulges 4, 5 decrease up to a line 6 of separation of the cheeks 2, 3 from each other and curl back towards this line of separation to together form a groove 7. This groove 7 represents an additional security against turning from torques in the axis 11 of the shank body 1 since a fitting shoulder usually remains upon rasping of a cavity in the bone tissue. The rasping in the bone and the bulges 4, 5 on the cheeks 2, 3 are matched to one another in steps by larger bulges 4, 5 also corresponding with larger angles of taper.

Figure 3:
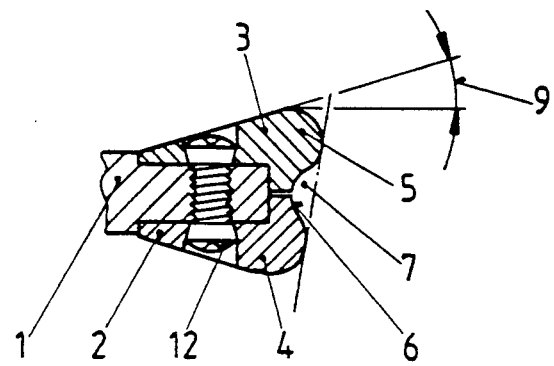
FIG. 3 illustrates a view taken on line III—III of FIG. 2.

Referring to FIG. 3, each bulge 4, 5 tapers inwardly from lateral to medial at an angle 9 of from 0° to 25° with the average angle of the taper corresponding to about 15° and depending upon the actual femur bone.

Figure 4:
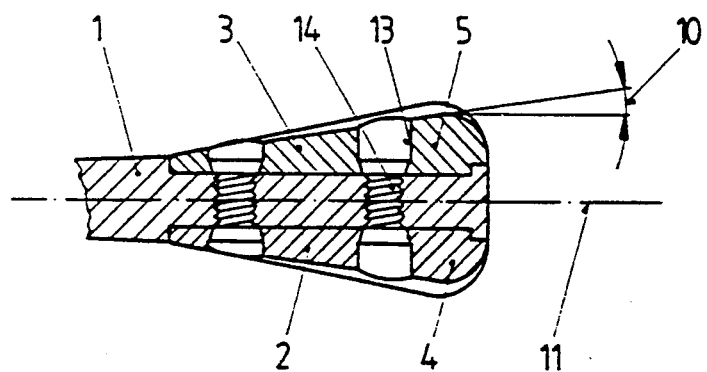
FIG. 4 illustrates a view taken on line IV—IV of FIG. 2.

Referring to FIG. 4, on the ventral and dorsal sides, each bulge 2, 3 tapers longitudinally inwardly from proximal to distal at an angle 10 of from 0° to 15° with an average angle being about 9° and also depending upon actual conditions.

Referring to FIG. 2, each bulge 2, 3 also tapers laterally inwardly from proximal to distal at an angle 8 of from 0° to 20° with the average angle of taper being 10°.

Through the adaptability of the two cheeks 2, 3 in steps and independently of one another, relatively large conical angles of taper 8, 9, 10 may be obtained. These angles of taper provide for a good distribution of the main load with low specific loadings upon the tissue growing in. Further, the relatively large angles of taper oppose a later sinking or settling in of the shank body 1. The conical tapering of the cheeks 2, 3 is chosen to be relatively steep in order to achieve a uniform distribution of the main load on the prosthesis over a cohesive area. To correspond with the graded sizes of the cheeks, the rasps (not shown) for generating the bone cavities are also graded and are guided during machining.

Figure 1:
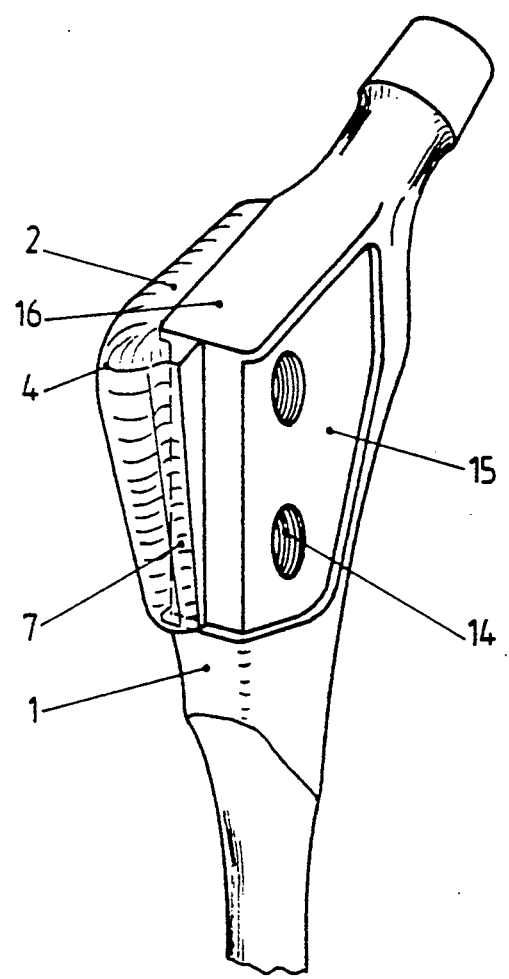
FIG. 1 illustrates a perspective view of a proximal end of a femur head prosthesis constructed in accordance with the invention with a cheek removed.

Referring to FIG. 1, each cheek 2 (only one of which is shown) can be mounted at the end 16 of the shank body 1 within a recess 15. As indicated, each recess 15 of the shank body 1 is provided with a pair of threaded bores or holes 14 to receive fixing screws 12 (see FIGS. 2 and 3) which serve to secure a cheek 2, 3 to the shank body 1. To this end, each cheek 2, 3 is provided with a counter bore 13.

The recesses 15 of the shank body 1 are sufficient so that the cheeks 2, 3 can be fitted in while at the same time having conically tapered regions which still have a reasonable thickness. Thus, the screws 12 need only transmit smaller forces from the cheeks 2, 3 in the direction of the axis 11 of the shank body 1.

As indicated in FIG. 1, each cheek 2, 3 has a surface remote from the shank body with a structure thereon of projections and recesses for promoting the growing in of bone tissue.

During implantation, the rasps (not shown) for machining the bone cavity are matched to the steps in the cheeks 2, 3 and are guided during machining in order to enable the most exact contact of the shank body 1 via the conical portions of the cheeks.

The invention thus provides a femur head prosthesis which can be readily adapted to the contours of a bone cavity in a femur in order to provide a relatively large primary anchorage with the bone tissue while, at the same time opposing a later settling in of the shank body.

What is claimed is:

1. A femur head prosthesis comprising
    a shank body for implanting in a femur; and
    a pair of cheeks removably fastened to opposite anterior and posterior sides of a proximal end of said shank body, each said cheek having a bulge extending laterally from said cheek and outwardly beyond said shank body and tapering in conically from a lateral side of said cheek to a medial side of said cheek and from proximal to distal.

2. A prosthesis as set forth in claim 1 wherein said cheeks define a longitudinally disposed groove between said bulges thereof.

3. A prosthesis as set forth in claim 1 wherein each cheek has a surface remote from said shank body with a structure thereon of projections and recesses.

4. A prosthesis as set forth in claim 1 wherein said shank body has a recess on each anterior and posterior side in said proximal end to receive a respective cheek therein.

5. A prosthesis as set forth in claim 1 wherein each bulge tapers laterally inwardly from proximal to distal at an angle of from 0° to 20°.

6. A prosthesis as set forth in claim 1 wherein each bulge tapers inwardly from lateral to medial at an angle from 0° to 25°.

7. A prosthesis as set forth in claim 1 wherein each bulge tapers longitudinally inwardly from proximal to distal at an angle of from 0° to 15°.

8. A kit for a femur head prosthesis comprising
    a shank body for implanting in a femur; and
    a plurality of cheeks for selective mounting to opposite anterior and posterior sides of a proximal end of said shank body, each said cheek having a bulge extending laterally from and extending outward said shank body and tapering in conically from a lateral side of said cheek to a medial side of said cheek and from proximal to distal.

* * * * *

UNITED STATES PATENT AND TRADEMARK OFFICE
CERTIFICATE OF CORRECTION

PATENT NO. : 5,092,900
DATED : March 3, 1992
INVENTOR(S) : Marchetti et al.

It is certified that error appears in the above-identified patent and that said Letters Patent is hereby corrected as shown below:

Column 1, line 47, change "With" to --with--;

Column 2, line 12, change "Which" to --which--;

Column 3, line 25, change "from said cheek and" to --from and--.

Signed and Sealed this

Ninth Day of November, 1993

Attest:

BRUCE LEHMAN

Attesting Officer           Commissioner of Patents and Trademarks